(12) United States Patent
Matsumura

(10) Patent No.: US 7,396,667 B2
(45) Date of Patent: Jul. 8, 2008

(54) ENZYMATIC DEPOLYMERIZATION PROCESS OF POLYLACTIC ACID, AND PRODUCING PROCESS OF POLYLACTIC ACID USING DEPOLYMERIZATION PRODUCT

(75) Inventor: Shuichi Matsumura, Yokohama (JP)

(73) Assignee: Keio University, Tokyo (JP)

( * ) Notice: Subject to any disclaimer, the term of this patent is extended or adjusted under 35 U.S.C. 154(b) by 268 days.

(21) Appl. No.: 10/523,688

(22) PCT Filed: Jul. 30, 2003

(86) PCT No.: PCT/JP03/09676

§ 371 (c)(1),
(2), (4) Date: Feb. 3, 2005

(87) PCT Pub. No.: WO2004/013217

PCT Pub. Date: Feb. 12, 2004

(65) Prior Publication Data

US 2005/0233425 A1    Oct. 20, 2005

(30) Foreign Application Priority Data

Aug. 5, 2002    (JP) ............................. 2002-227644

(51) Int. Cl.
C12P 7/62 (2006.01)
C12P 17/02 (2006.01)
C12P 17/08 (2006.01)
C12N 9/16 (2006.01)
C12N 9/20 (2006.01)

(52) U.S. Cl. .................. 435/135; 435/123; 435/124; 435/125; 435/126; 435/195; 435/196; 435/198

(58) Field of Classification Search ................. 435/135, 435/123, 124, 125, 126, 195, 196, 198
See application file for complete search history.

(56) References Cited

U.S. PATENT DOCUMENTS 6,255,451 B1    7/2001   Koch et al.

FOREIGN PATENT DOCUMENTS

| JP | A 11-35662 | 2/1999 |
| JP | A 2001-178483 | 7/2001 |
| JP | A 2001-224392 | 8/2001 |
| JP | A 2002-17385 | 1/2002 |
| JP | A 2002-320499 | 11/2002 |
| JP | A 2003-79388 | 3/2003 |

OTHER PUBLICATIONS

Mauduit et al Abstract "Hydrolytic degradation of films prepared from blends of high and low molecular weight poly(DL-lactic acid)s" Journal of Biomed Materials Res vol. 30 Iss 2 pp. 201-207 1998.*
Sakai et al Abstract "Isolation of a Thermophilic Poly-L-Lactide Degrading Bacterium from Compost and its Enzymatic Charatererization" Jour Biosci & Bioeng vol. 92 No. 3 p. 298-300 (2001).*
Williams., "Enzymic hydrolysis of polylactic acid," MEP ltd., vol. 10, No. 1, pp. 5-7, 1981.
Matsumura et al., "Novel Ring-Opening Polymerization of Lactide by Lipase," Macromol. Symp. 130, pp. 285-304, 1998.

* cited by examiner

Primary Examiner—Herbert J Lilling
(74) Attorney, Agent, or Firm—Oliff & Berridge, PLC

(57) ABSTRACT

A depolymerizing process of polylactic acid, wherein the polylactic acid is depolymerized in the presence of a hydrolase in an organic solvent or a supercritical fluid, thereby producing a re-polymerizable oligomer. A producing process of polylactic acid, wherein the re-polymerizable oligomer obtained by the above-mentioned depolymerization process is polymerized in the presence of a hydrolase or a polymerization catalyst.

9 Claims, 14 Drawing Sheets

FIG.7
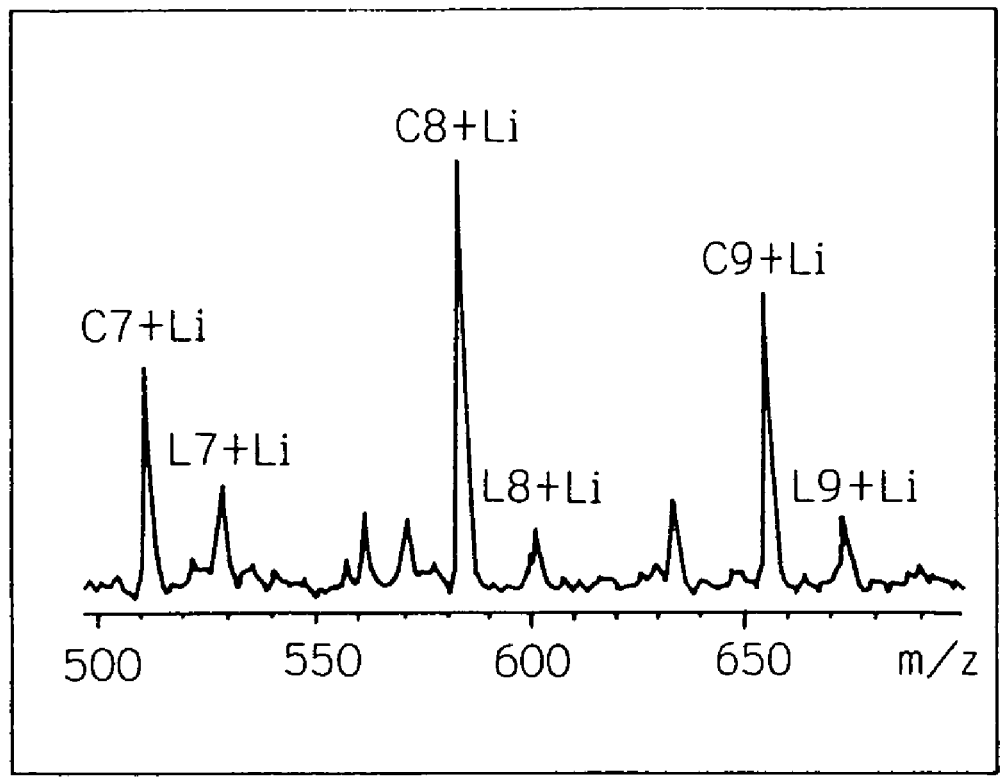
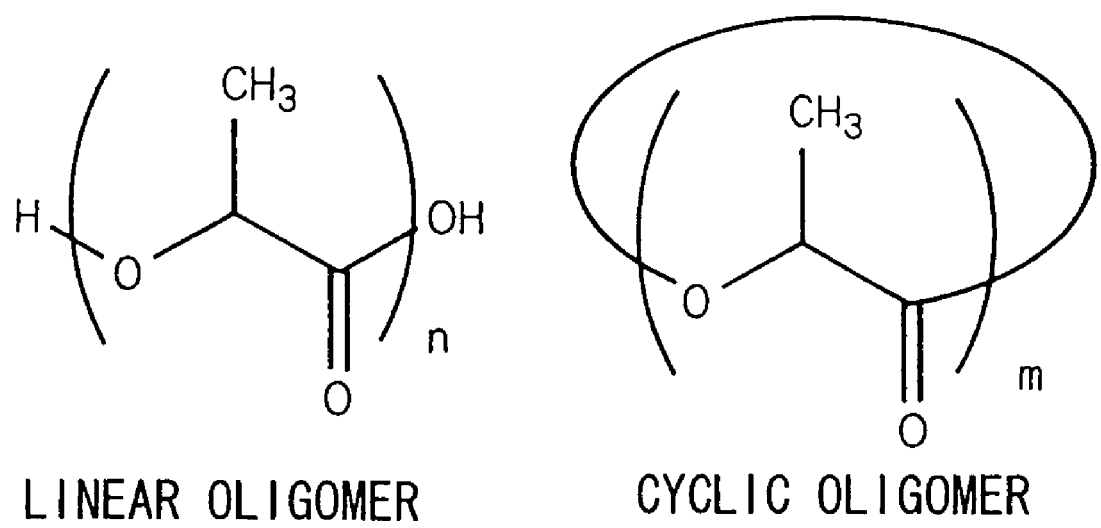
LINEAR OLIGOMER         CYCLIC OLIGOMER

US 7,396,667 B2

ENZYMATIC DEPOLYMERIZATION PROCESS OF POLYLACTIC ACID, AND PRODUCING PROCESS OF POLYLACTIC ACID USING DEPOLYMERIZATION PRODUCT

TECHNICAL FIELD

The present invention relates to a complete-cycle polymer chemical recycling process of using a hydrolase to depolymerize polylactic acid and polylactic acid-based copolymers, which are biodegradable plastics that have recently acquired high expectations, thereby yielding a re-polymerizable oligomer, and then re-polymerizing this to produce polylactic acid.

BACKGROUND ART

In recent years, with the critical situation of the worsening of the global environment with global warming and the like, the construction of systems with sustainable use of materials has been accelerated from the viewpoint of using effectively the limited carbon resources and conserving limited energy resources. In the case of polymer products, after use the products are reused as they are (examples of this case include the conversion of PET bottles to fibrous material), or recycled or discarded. For recycling processes, material recycling processes, chemical recycling processes, thermal recycling processes, and the like are used. However, material recycling processes involve a deterioration in quality, such as a drop in molecular weight, chemical recycling processes consume much energy, and thermal recycling process generate a large amount of carbon dioxide gas. Thus, each of these processes involve problems.

From the viewpoint of effective use of carbon resources, the ideal is that products are finally restored to the raw materials thereof by chemical recycling processes. Regarding chemical recycling processes, the recovery of monomers by depolymerization reactions, and recovery of monomers as raw materials by chemically decomposition reactions are known. However, in the case of performing depolymerization based on chemical decomposition or thermal decomposition, both terminals of a generated low molecular weight compound are irregular. It is therefore impossible to re-polymerize such compounds as they are, and it is necessary to conduct isomerization reactions, purification thereof or some other operations. For example, when polyester is hydrolyzed at high temperature and high pressure in the presence of NaOH, carboxylic acid yielded is present as a Na salt thereof. Thus, this acidity must be neutralized. Accordingly, the processes consume much energy, and cause the discharge of inorganic salts (such as NaCl), and other problems. Thus, the processes impose large loads upon environment, and are generally unprofitable.

Apart from the viewpoint of reuse, attention has been paid to the so-called biodegradable polymers, which are degraded by bacteria and the like in the ground, as polymers imposing only small loads on environment. Various such biodegradable polymers have been suggested. For example, for biodegradable polymers biodegradable polyesters are known. Typical examples of biodegradable polyesters produced by chemical synthesis include polycaprolactone (PCL), polylactic acid (PLA), polyhydroxybutyric acid (PHB), and aliphatic polyesters made from diol and succinic acid, such as polyethylene succinate, polybutylene succinate (PBS) and polybutylene succinate/adipate copolymer (PBS/A). Among these, as well as polylactic acid and polycaprolactone, polybutylene succinate (PBS) has been investigated in an attempt to make it practicable as a typical chemically-synthesized biodegradable plastic, since PBS can be obtained from 1,4-butanediol and succinic acid by a petrochemical industrial process.

Among the above-mentioned examples, poly(L-lactic acid) (PLA) is a polymer yielded by polymerizing lactic acid, which is obtained by fermenting corn starch, or the like, which is a renewable resource. It can be said that this polymer is a low environment load polymer, which does not cause a direct increase in the total amount of carbon dioxide gas even if the polymer is finally biodegraded or burned up. Lactic acid or a dimer thereof, which is the raw material of the polymer, has already been produced with a high efficiency by research and development over many years.

Polylactic acid is a biodegradable plastic which has strength equivalent to that of polyethylene or polystyrene, has a higher transparency than other biodegradable plastics, and is superior in weather resistance, heat resistance, workability and the like. Polylactic acid has already been put to practical use such as in covering materials for agriculture, fibers, earth-retaining netting, weed-preventing bags and the like. Accordingly, polylactic acid is a biodegradable plastic that has currently been developed furthest towards practical use.

Polylactic acid is degraded to water and carbon dioxide with several years in the ground, or in a short period in compost. Therefore, covering materials and the like for agriculture, which are used outdoors, can be left as they are after they have been used. However, polylactic acid has a considerably lower biodegradability than polycaprolactone or polyhydroxybutyric acid. Thus, there is the fear that a large amount of polylactic acid left outdoors may cause a new environmental problem.

There is a chemical recycling process in which polylactic acid is thermally decomposed to regenerate the monomer thereof. This process requires a high temperature of 270° C. or higher, and consumes much energy. Thus, it is difficult to say that this process is superior in recycling. Although polylactic acid can be obtained from a renewable resource, it is impossible to ignore energy applied to the production thereof, including the cultivation of plants for producing starch as the raw material, the harvesting thereof and production by fermentation and the like. Moreover, the raw materials of a biodegradable polymer such as polylactic acid are not recovered, although the biodegradable polymer imposes only a small load on the environment. Accordingly, the process does not fall under the category of complete-cycle type of reuse, wherein carbon resources are effectively used. Thus, it is hard to say that the process is an ideal polymer-degrading process.

Accordingly, a polymer producing/degrading process can be constructed, which is one of both low energy consumption and is also a complete-cycle type, if the following can be attained: a polymer can be degraded into a low molecular weight compound without using high energy, such as petroleum energy, like biodegradable polymers; the low molecular weight compound can be effectively utilized; and, if desired, the original polymer can be obtained from the low molecular weight compound without similarly consuming any high energy.

Incidentally, Japanese Patent Application National Publication (Laid-Open) No. 2001-512504 describes, as a process for degrading a biodegradable polymer a process of degrading various biodegradable polymers, such as aliphatic or partially-aromatic polyesters, thermoplastic aliphatic or partially-aromatic polyester urethanes which may contain a urethane group, aliphatic-aromatic polyester carbonates and/or aliphatic or partially-aromatic polyester amides, by use of an enzyme such as lipase in an aqueous enzyme solution in which a buffer may be contained. However, the degrading technique described in this publication is a technique for degrading a biodegradable polymer rapidly in an aqueous solution by using an enzyme, and, for example, for the use in a method of degrading and removing a biodegradable polymer from a complex of the biodegradable polymer and a different useful material (such as a metal), thereby recovering the useful material easily. The main aim thereof is not to reuse products generated after the degradation. It is also difficult to use the product decomposed by this process for re-polymerization or the like.

The above-mentioned publication states that fine particles of polylactic acid, which is a biodegradable polymer, is degraded in the presence of a specific lipase in a potassium phosphate buffer solution. However, it is a well-known fact that polylactic acid is not degraded under ordinary conditions even if microorganisms are present therein and polylactic acid is not degraded by microorganisms without, for example, conditions of high-temperature and high-humidity. It is thought that this is because polylactic acid is first hydrolyzed at high temperature and high humidity, so that a fall in the molecular weight occurs, and it is not until the stage at which the hydrolysis advances that polylactic acid starts to be degraded by the participation of microorganisms (a two-stage reaction) (J. Lunt, Polymer Degradation and Stability 59, 145-152 (1998)). It appears that the lipase degradation of polylactic acid in a potassium phosphate buffer solution, described in the above-mentioned publication, is based on the following: polylactic acid is first hydrolyzed so that a fall in the molecular weight thereof occurs since polylactic acid is made into very fine powder, and lipase acts on the low molecular weight polylactic acid. (The only enzyme capable of degrading high molecular weight polylactic acid which is known is protease K.)

The rapid degradation of polylactic acid in compost by microorganisms is caused by the occurrence of a two-stage reaction as described above, since conditions of high temperature and high humidity are maintained in the compost.

Accordingly, it is considered that no enzyme other than protease K can be caused to act directly on polylactic acid so as to degrade the acid. The mainstream of practical research is about degradation of polylactic acid in compost. Currently, research into causing enzymes to directly act on polylactic acid to degrade the acid is not being carried out, excepting research in which the degradation by use of the above-mentioned protease K is used for simplified evaluation of biodegradability. Additionally, research based on a concept that polylactic acid is depolymerized with an enzyme to recover a re-polymerizable oligomer has not yet been undertaken. Accordingly, there has not yet been suggested any chemical recycling process of depolymerizing polylactic acid with an enzyme to yield a re-polymerizable oligomer.

Correspondingly, the inventor of the present invention previously suggested a process for depolymerizing a polymer with an enzyme, wherein a depolymerization product generated by depolymerizing the polymer has re-polymerizability. Japanese Patent Application Laid-Open (JP-A) No. 2002-17385 describes a depolymerizing process of a caprolactone polymer with a hydrolase. By this depolymerization, dicaprolactone is produced in a high yield, and the produced dicaprolactone can be re-polymerized with an enzyme. Japanese Patent Application No. 2001-131768 relates to a process of depolymerizing polyalkylene alkanoate or poly(3-hydroxyalkanoate) in the presence of a hydrolase to produce re-polymerizable oligomer(s) including, as main component(s), cyclic oligomer(s). Furthermore, Japanese Patent Application No. 2002-193114 relates to a process of depolymerizing polyester or polycarbonate in the presence of a hydrolase in a supercritical fluid. A cyclic oligomer can be re-polymerized with an enzyme in a supercritical fluid.

These polymers are conventionally well known as biodegradable polymers which are easily degraded by microorganisms, and the behavior thereof to microorganisms is greatly different from that of polylactic acid.

DISCLOSURE OF THE INVENTION

The present invention has been made on the basis of the imperatives as described above. An object thereof is to provide a complete-cycle method of use of polylactic acid, wherein polylactic acid is depolymerized with an enzyme to yield a re-polymerizable oligomer and the re-polymerizable oligomer is re-polymerized to yield polylactic acid.

The above-mentioned issues are solved by providing the following depolymerizing process and re-polymerizing process.

A first depolymerizing process of the invention is a process wherein polylactic acid is depolymerized in the presence of a hydrolase in an organic solvent, thereby producing a re-polymerizable oligomer.

A second depolymerizing process of the invention is a process wherein polylactic acid is depolymerized in the presence of a hydrolase in a supercritical fluid, thereby producing a re-polymerizable oligomer.

A first re-polymerizing process is a process wherein the re-polymerizable oligomer obtained by the first or second depolymerization process is polymerized in the presence of a hydrolase.

A second re-polymerizing process is a process wherein the re-polymerizable oligomer obtained by the first or second depolymerization process is polymerized in the presence of a polymerization catalyst.

BRIEF DESCRIPTION OF THE DRAWINGS

FIG. 7 is a graph showing the MALDI-TOF MS of a depolymerization product in Example 6.

BEST MODE FOR CARRYING OUT THE INVENTION

Figure 1:
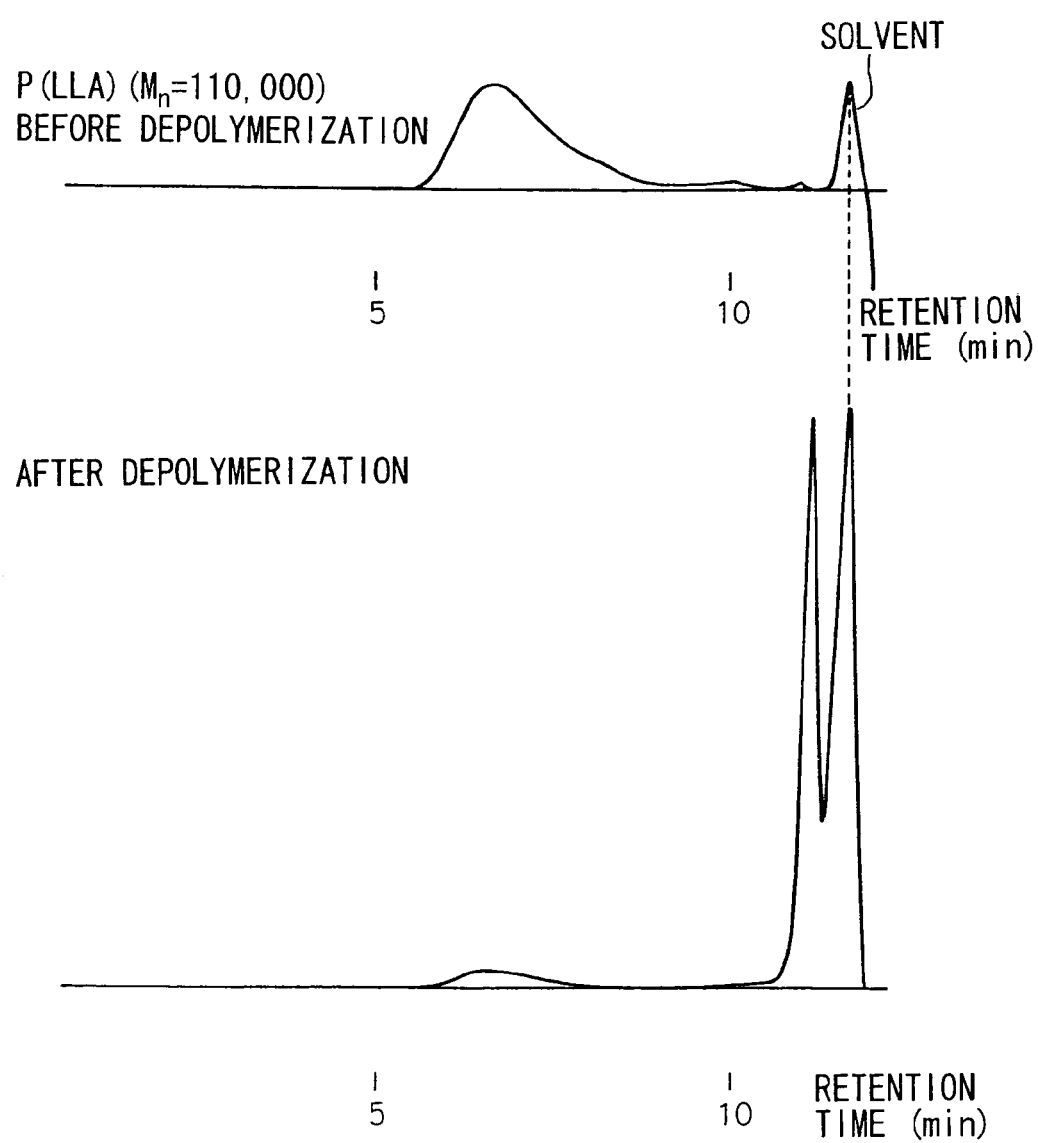
FIG. 1 is a graph showing a change in GPC before and after depolymerization in Example 1.

The inventor of the present invention has made eager researches to aim a complete-cycle type recycling of polylactic acid and overthrown common knowledge about conventional enzymatic degradation of polylactic acid and found out that polylactic acid can be depolymerized into an oligomer with an enzyme and further the generated oligomer is a re-polymerizable oligomer mixture and can easily be re-polymerized into polylactic acid. The generated oligomer is a mixture composed of various low molecular weight compounds. The re-polymerization of this mixture makes it possible to yield polylactic acid. The re-polymerization may be chemically synthetic polymerization, that is, polymerization using a catalyst besides polymerization using a hydrolase.

The depolymerization of polylactic acid and the polymerization of the invention, using a hydrolase, may be conducted by a simple operation by use of one pot, is mild in reaction conditions, and consumes only low energy. In the case that the depolymerization is conducted by chemical degradation or thermal degradation, both ends of a generated low molecular weight compound is irregular and such compound cannot be re-polymerized into a polymer. However, according to the depolymerization of the invention, a re-polymerizable oligomer mixture is easily generated. The oligomer mixture is easily re-polymerized into a polymer in the presence of a hydrolase or in a chemically synthetic manner.

This re-polymerizable oligomer mixture is easily collected without any especially complicated purifying step. Furthermore, the hydrolase used to conduct the depolymerization or the polymerization can be collected and repeatedly used. The invention has an advantageous point that a decrease in the activity of the enzyme is not substantially caused at this time. In the case that polylactic acid is a copolymer, a re-polymerizable oligomer mixture obtained by depolymerizing the polylactic acid copolymer is re-polymerized, thereby making it possible to regenerate a polymer having the same composition as the original polylactic acid copolymer.

Accordingly, the invention makes it possible to construct a complete-cycle type polymer material using system which is of environmentally acceptable and is capable of reusing carbon resources completely.

The following details the depolymerization process of polylactic acid of the invention and the process for re-polymerizing the oligomer produced by the depolymerization to obtain polylactic acid.

[Depolymerization Process of Polylactic Acid]

The depolymerization process of polylactic acid of the invention is characterized by depolymerizing polylactic acid in the presence of a hydrolase in an organic solvent.

As the polylactic acid used in the depolymerization of the invention, there may be used polylactic acid or a polylactic acid copolymer used in a formed product, such as a film or fiber, or others without any especial limitation. Examples of the homopolymer include poly(L-lactic acid), poly(DL-lactic acid), syndiotactic poly(DL-lactic acid), and atactic poly(DL-lactic acid).

The polylactic acid copolymer may be a product obtained by copolymerizing, into polylactic acid, a comonomer which can be copolymerized with lactide and which generates a bond that is receptive to the action of a hydrolase as described above. Examples of the comonomer include medium-sized cyclic lactones to macrocyclic lactones, such as β-propiolactone, β-butyrolactone (β-BL), ε-caprolactone (ε-CL), 11-undecanolid and 12-undecanolid; cyclic carbonate monomers such as trimethylenecarbonate (TMC) and methyl-substituted trimethylenecarbonate, and oligomers thereof; cyclic-ester oligomers; hydroxy acids such as recinoleic acid, and esters thereof; linear carbonate oligomers; linear ester oligomers; ester-carbonate oligomers; and ester-ester oligomers. These comonomers are preferably contained in the copolymer in an amount of 50% or less by mole. If an enzyme or the like is appropriately selected when the polylactic acid copolymer is depolymerized, the composition ratio of the comonomers in the oligomer can be made substantially equal to the composition ratio of the comonomers in the polylactic acid copolymer. Consequently, by re-polymerizing a re-polymerizable oligomer mixture obtained by depolymerizing the polylactic acid copolymer, a polymer having the same composition as the original polylactic acid copolymer can be regenerated. In conventional recycling processes, in order to obtain a polymer having the same composition as an original polymer, it is indispensable that respective monomers thereof are recovered and these are polymerized in the same manner as the original polymer. This is technically difficult, and increases costs largely. Thus, the conventional processes are not regarded as practical processes.

The molecular weight (Mn) of polylactic acid and any polylactic acid copolymer, (which may be referred to merely as polylactic acid hereinafter), is not particularly limited. In general, the molecular weight is suitably about 10,000 to 1,000,000.

The depolymerization of polylactic acid of the invention is conducted by dissolving the polylactic acid into a suitable solvent, adding thereto a hydrolase to prepare a depolymerizing solution, and causing the polylactic acid to undergo depolymerization-reaction for an appropriate time while keeping the solution at an appropriate temperature and preferably stirring the solution.

As the enzyme used in the depolymerization of the invention, any hydrolase which acts on an ester bond is used without any especial limitation. The enzyme may be immobilized or may not be immobilized. From the viewpoint of the recovery of an oligomer and the reuse of the enzyme, the immobilized enzyme is favorable. The hydrolase is preferably lipase for its easy availability and thermal stability. Particularly preferable are lipase derived from *Candida antaratica*, and lipase derived from *Rhizomucor miehei*. An example of the immobilized enzyme derived from *Candida antaratica* is "Novozym 435 (trade name)" by Novozymes Japan Ltd., and an example of lipase derived from *Rhizomucor miehei* is "Lipozyme RM IM (trade name)" by Novozymes Japan Ltd. Besides this, "Bioprase (trade name)", which is a protease derived from *Bacillus subtilis*, by Nagase ChemteX Corporation may also be used as the hydrolase in the same manner.

The added amount of the enzyme (including an immobilized enzyme), in the depolymerization of the invention, is at least 0.05%, preferably 0.1% or more by mass of polylactic acid. If the amount is less than 0.05% by mass, the rate of the reaction lowers remarkably. Thus, the above-mentioned added amount is suitable. If the added amount of the enzyme is made large, the reaction becomes faster. However, a case in which the amount is too large is unpractical. Thus, the amount is suitably at most about 50% by mass. (In the case of the immobilized enzyme, the added amount of the enzyme usually corresponds to 1 to 1000% by mass of polylactic acid.)

Any solvent in which polylactic acid can be dissolved at least partly and further in which the enzyme is not inactivated, such as o-xylene, toluene, acetonitrile, 1,4-dioxane, tetrahydrofuran, hexane or the like, may be used without any limitation. It has been confirmed that xylene and toluene are particularly useful for the depolymerization. Combinations of various solvents at a specific composition ratio make it possible to make the conversion ratio higher than the use of any one of the organic solvents alone. For example, although it is not much preferred to use chloroform alone (the enzyme is inactivated), the conversion ratio is made better in the case of mixing a small amount of chloroform with hexane than in the case of 100% hexane. The addition of hexane to o-xylene or toluene makes the conversion ratio better than the use of o-xylene or toluene only.

Water is not preferred since water causes the enzymatic degradation of the resultant oligomer. Since the solubility of polylactic acid in organic solvent is relatively low, some approaches are preferably carried out, for example: a mixed solvent system is used; or an easily-soluble solvent such as chloroform is first used to dissolve polylactic acid therein, a solvent as described above is added thereto, and then chloroform is distilled off (in order not to inactivate the enzyme).

The concentration of the polylactic acid contained in the depolymerizing reaction solution is generally 0.1 to 100 g/l, and suitably 0.5 to 50 g/l. If the concentration is less than 0.1 g/l, the yield itself is not particularly low but the amount of the resultant oligomer is not sufficiently secured with ease. If the concentration is more than 100 g/l, the conversion ratio to the oligomer lowers. Thus, the above-mentioned range is preferable.

Water is unsuitable as the solvent. However, when water is not present at all in the depolymerization system, the activity of the hydrolase is not kept. It is therefore preferable to add a very small amount of water to the system. In the case that the enzyme itself holds water, no water needs to be added. The water content for keeping the activity of the enzyme is about 0.05 to 100% by mass of polylactic acid in the reaction system.

The temperature for the depolymerization is from 30 to 120° C., preferably from 40 to 100° C. If the temperature is lower than 30° C., the depolymerization rate is small, and if the temperature is over 120° C., the enzyme is easily inactivated. Thus, the above-mentioned range is suitable.

The reaction time for the depolymerization is desirably about 6 to 48 hours. If the time is shorter than 6 hours, the depolymerization does not advance sufficiently, on the other hand, even if the depolymerization is conducted for 48 hours or more, the depolymerization does not advance any more and it is economically unfavorable. Thus, the above-mentioned range is suitable.

In the invention, a supercritical fluid can be used as the depolymerizing solvent. The supercritical fluid used as the solvent may be carbon dioxide, fluoroform ($CHF_3$), or the like. Carbon dioxide is harmless, inexpensive and noninflammable, and the critical-point thereof is about 31° C., at 7.4 MPa. Thus, carbon dioxide easily reaches the critical point and is suitable as the medium used in the depolymerization and the polymerization of the invention. Carbon dioxide is suitable for handling relatively hydrophobic molecules, and fluoroform is suitable for handling relatively hydrophilic molecules.

The depolymerization of polylactic acid is conducted by putting the polylactic acid and a hydrolase into a pressure-resistant reaction tube, pouring liquefied carbon dioxide thereinto while pressuring the carbon dioxide with a liquid-feeding pump, so as to make the carbon dioxide into a supercritical state, and then causing the polylactic acid to undergo depolymerization-reaction for a suitable time while keeping the supercritical carbon dioxide at a suitable temperature and preferably stirring the solution. The temperature of the supercritical carbon dioxide at the time of the depolymerization is preferably about 40 to 90° C., and the pressure is preferably about 7.2 to 30 MPa. The reaction time for the depolymerization is desirably at least 3 hours. The upper limit of the reaction time is not particularly limited. However, if the reaction is conducted at 48 hours or more, the depolymerization does not advance any more, and it is economically unfavorable.

The concentration of the polylactic acid in the supercritical fluid is preferably set into the range of about 0.5 to 50 g/l. The amount of the hydrolase added to the polylactic acid is suitably 0.05 to 50% by mass (about 1 to 1000% by mass in the case of the immobilized enzyme). The water content, for keeping the activity of the enzyme, in the reaction system is suitably about 0.1 to 100% by mass of the polylactic acid.

In the invention, the depolymerization rate is improved by adding a small amount that is about 0.05 to 5% by volume of ethanol as an organic solvent to the organic solvent or supercritical fluid as described above, examples of the organic solvent including o-xylene, toluene, acetonitrile, 1,4-dioxane, tetrahydrofuran and hexane.

Regarding the re-polymerizable oligomers obtained by the depolymerization of the invention, a re-polymerizable oligomer mixture including, as a main component, a cyclic oligomer is obtained in the case that no ethanol is added to the organic solvent or supercritical fluid. The re-polymerizable oligomers including, as a main component, a cyclic oligomer are monomers suitable for enzymatic polymerization, and are easily polymerized under mild conditions by a simple operation with an enzyme so that the original polymer can easily be produced. At this time, the oligomer can be copolymerized with a different monomer. The cyclic oligomer can be polymerized not only in the manner using an enzyme but also in a chemically synthetic manner, that is, in the presence of a polymerization catalyst. At this time, the oligomer can be polymerized by use of no solvent, and the time for the polymerization is also shortened. Further, since the polymerization of the cyclic oligomer is ring-opening polymerization and so generates no released components such as water, it is therefore unnecessary to discharge these from the reaction system. Accordingly, the operation of the polymerization reaction is simple and no exhaust equipment is needed. Additionally, simultaneous molding can also be attained.

When ethanol is added to the organic solvent or supercritical fluid as described above, a linear re-polymerizable oligomer wherein one of terminals is ethyl-esterified is obtained as a main component.

The above-mentioned re-polymerizable oligomer mixture including, as a main component, a cyclic oligomer includes therein a linear oligomer as a minor component. However, the oligomer is easily re-polymerized in the presence of a hydrolase or in a chemically synthetic manner so as to be converted to a polymer.

[Re-polymerization of Depolymerization Product]

The re-polymerizable oligomer mixture obtained by the depolymerization of the invention can easily be re-polymerized by use of a hydrolase or a chemical catalyst. At this time, a copolymer having a varied polymer physical property can be produced by adding, to the re-polymerizable oligomer mixture, one or more monomers or oligomers selected from cyclic lactone monomers or oligomers, cyclic or linear carbonate monomers or oligomers, cyclic or linear ester oligomers, hydroxy acids, and hydroxy acid esters.

The re-polymerization using a hydrolase is conducted by dissolving the re-polymerizable oligomer mixture into a suitable solvent, adding thereto a hydrolase to prepare a polymerizing solution, and then causing the mixture to undergo polymerization-reaction for a suitable time while keeping the solution at an appropriate temperature and preferably stirring the solution. As the hydrolase, the hydrolase used in the depolymerization can be used in the same manner.

In the polymerization of the re-polymerizable oligomer mixture of the invention, the added amount of the hydrolase (including an immobilized enzyme) is about 0.05 to 50% by mass of the re-polymerizable oligomer mixture (about 1 to 1000% by mass in the case of the immobilized enzyme), and preferably about 0.1 to 20% by mass. If the amount is less than 0.05% by mass, the polymerization rate lowers and the monomer conversion ratio also lowers easily, and if the amount is more than 50% by mass, the molecular weight of the resultant polymer easily becomes low. Thus, the above-mentioned range is suitable.

As the solvent in which the re-polymerizable oligomer mixture is dissolved, a solvent used at the time of the depolymerization is used in the same manner.

The temperature for the polymerization may be 30 to 120° C., in particular preferably 50 to 90° C. If the temperature is lower than 30° C., the reaction rate becomes small, and if the temperature is higher than 120° C., the enzyme is inactivated. Thus, the polymerization temperature is suitably in the above-mentioned range.

The reaction time is suitably 1 to 72 hours. If the time is shorter than 1 hour, the reaction does not advance sufficiently. If the reaction is conducted for 72 hours or more, the polymerization does not advance any more, and it is economically unfavorable. Thus, the above-mentioned time range is preferable.

An ordinary process for polymerizing polylactic acid can be applied to the process using a chemical catalyst.

When the re-polymerizable oligomer mixture of the invention is re-polymerized, a supercritical fluid can be used as a reaction medium in the same way as in the case of the depolymerization. The concentration of the re-polymerizable oligomer mixture in the supercritical fluid is preferably about 0.1 to 50 g/l, in particular preferably about 1 to 20 g/l.

The amount of the hydrolase added to the re-polymerizable oligomer mixture is suitably about 0.1 to 50% by mass. The temperature for the polymerization can be set into the range of about 30 to 90° C., and the time for the polymerization is suitably about 1 to 48 hours.

In the depolymerization and the polymerization processes using a supercritical fluid, the supercritical fluid is used as a reaction medium; therefore, the reaction medium can easily be discharged outside the system only by returning the pressure in the system to normal pressure after the reaction. Consequently, a product is easily separated from the system. The discharged reaction medium can be recovered and reused. In particular, in the case that carbon dioxide is used as the supercritical fluid, it is not feared that environment is polluted even if the solvent leaks outside the system.

Furthermore, the reaction efficiency of the depolymerization and the polymerization is equivalent to that of the depolymerization and the polymerization using an ordinary organic solvent.

EXAMPLES

The present invention is more specifically described by way of the following examples. However, the invention is not limited to these examples. In the following examples, the wording "conversion ratio" means a ratio (% by mass) of an oligomerized polymer in a polymer as raw material.

Example 1

Depolymerization of poly(L-lactic acid) (PLLA)

There were weighed 150 mg of PLLA (Mn=110,000), 150 mg of an immobilized enzyme, Novozym 435, and 300 ml of o-xylene, and then they were put into a small pressure-resistant test tube with a screw cap, in which a magnetic stirrer was put. The tube was purged with argon, and then the solution was stirred at 100° C. for a day to depolymerize PLLA. Next, thereto was added a small amount of chloroform, and then the immobilized lipase which was insoluble was filtrated off. An evaporator was used to concentrate the solvent from the filtrate under reduced pressure to yield oligomers including, as main components, cyclic oligomers, at a conversion ratio of 90%.

Figure 2:
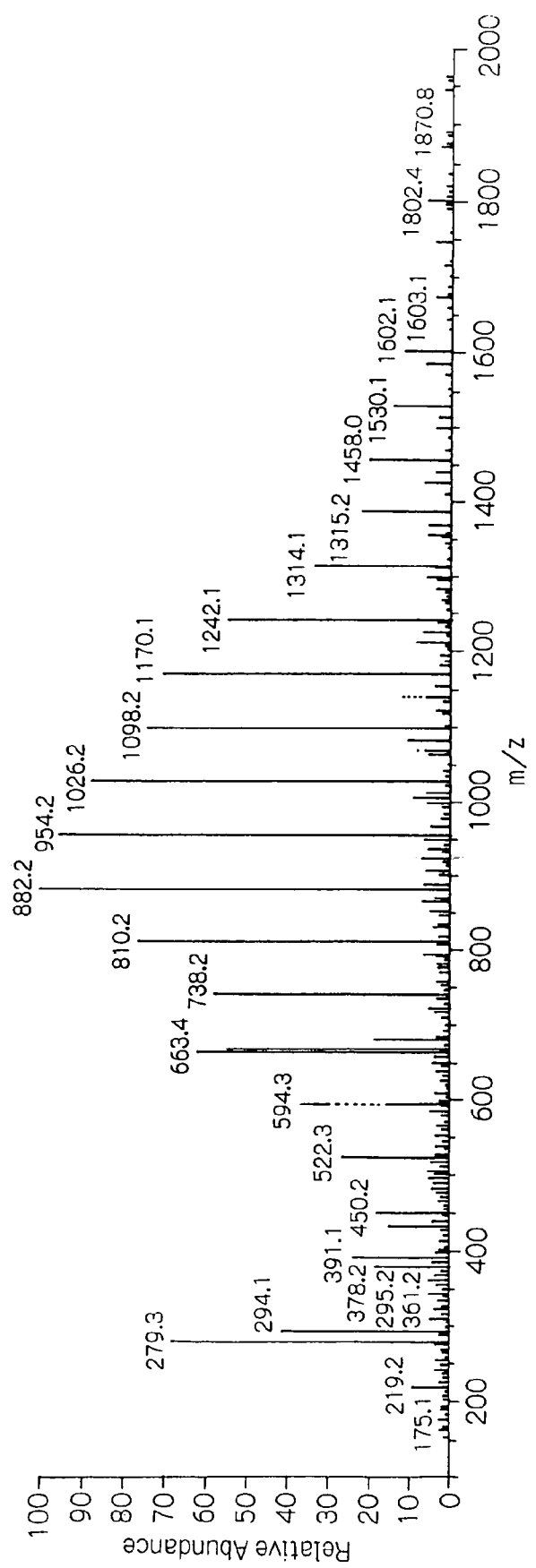
FIG. 2 is a graph showing the APCI MS [cyclic $M^{30}+H_2O$ (18)] of a depolymerization product in Example 1.
Figure 3:
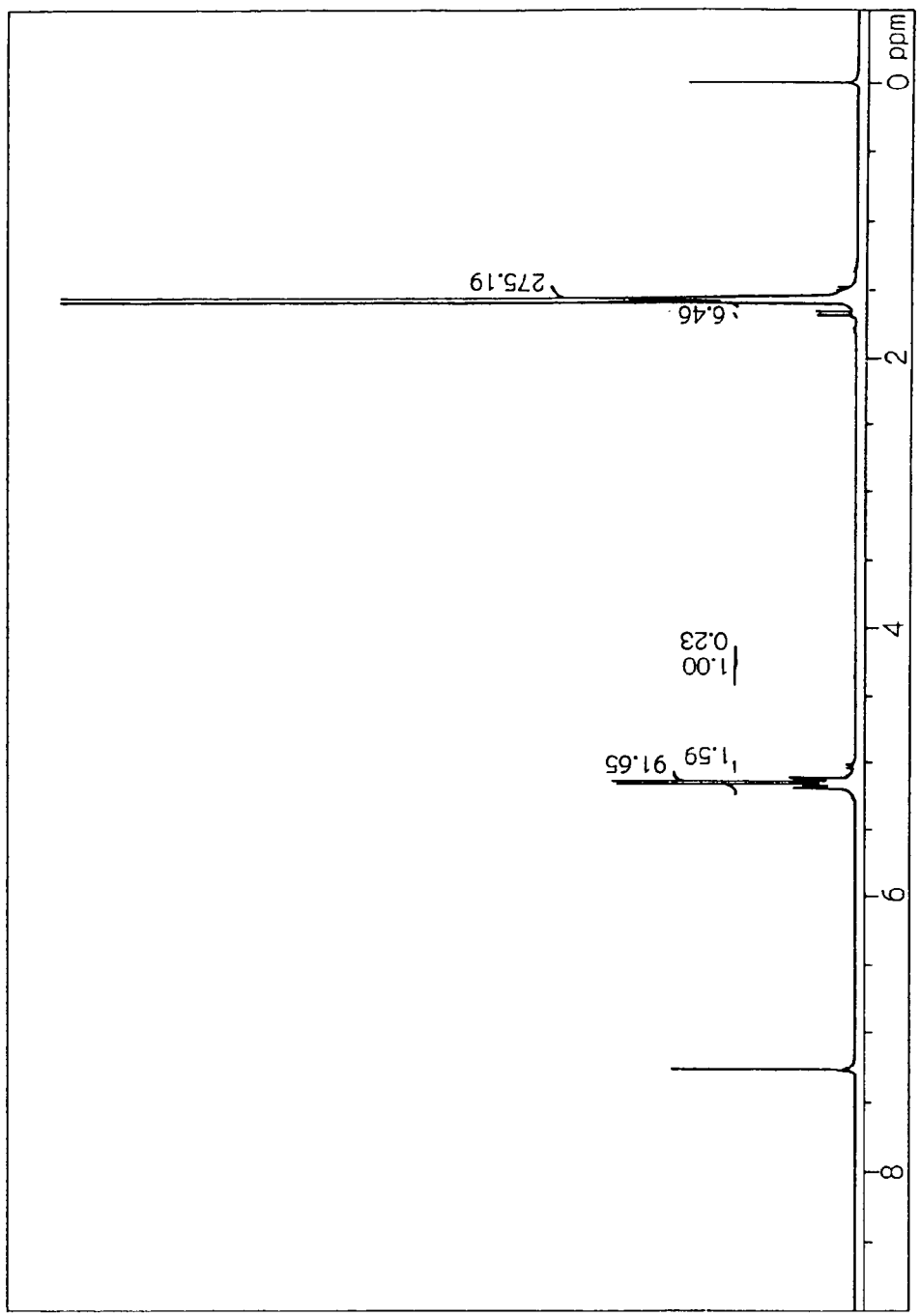
FIG. 3 is a graph showing the $^1$H-NMR of the depolymerization product in Example 1.

FIG. 1 shows GPCs before and after the depolymerization, and FIG. 2 shows an APCI MS [cyclic $M^+ + H_2O$ (18)] which was analyzed in the course of the depolymerization reaction. It was detected that the number of lactic acid units in the cyclic oligomer, which was obtained by use of a calibration curve from the GPCs of FIG. 1, was about three. It was also confirmed that the produced oligomers were cyclic from the fact that degradation products of from a low molecular weight to a relatively high molecular weight were cyclic lactic oligomers in the degradation step as illustrated in the graph of FIG. 2 and the fact that no peak identified as a terminal group was recognized from the $^1$H-NMR of final degradation products shown in FIG. 3.

$^1$H-NMR: (300 MHz, $CDCl_3$) δ=1.49-1.52 ($CH_3$), 5.05-5.13 ppm (CH)

Example 2

Depolymerization of poly(L-lactic acid) (PLLA)

Ten milligrams of PLLA (Mn=110,000) was dissolved into 0.5 ml of chloroform. Next, thereto was added 2 ml of o-xylene. Thereafter, chloroform was distilled off under reduced pressure. Thereto was added 90 mg of the immobilized enzyme, Novozym 435. This was put into a small pressure-resistant test tube with a screw cap, in which a magnetic stirrer was put. The tube was purged with argon, and then the solution was stirred at 65° C. for 2 days to yield oligomers including, as main components, cyclic oligomers, at a conversion ratio of 18%.

Example 3

Depolymerization of poly(L-lactic acid)

Ten milligrams of PLLA (Mn=110,000) was dissolved into 0.5 ml of chloroform. Next, thereto was added 2 ml of o-xylene. Thereafter, chloroform was distilled off under reduced pressure. Thereto were added 50 μL of water and 10 mg of Bioprase. This was put into a small pressure-resistant test tube with a screw cap, in which a magnetic stirrer was put. The tube was purged with argon, and then the solution was stirred at 40° C. for 2 days to yield oligomers including, as main components, cyclic oligomers, at a conversion ratio of 19%.

Example 4

Depolymerization of poly(DL-lactic acid) (PDLLA)

There were weighted 10 mg of PDLLA (Mw=140,000), 30 mg of an immobilized enzyme, Lipozyme RM IM, and 2 ml of each of mixed organic solvents wherein chloroform, toluene or o-xylene was mixed with hexane to have various composition ratios, and each of them was put into a small pressure-resistant test tube with a screw cap, in which a magnetic stirrer was put. The tube was purged with argon, and then the solution was stirred at 60° C. for a day to depolymerize PDLLA. Next, thereto was added a small amount of chloroform, and then the immobilized lipase which was insoluble was filtrated off. An evaporator was used to concentrate the solvent from the filtrate under reduced pressure to yield oligomers including, as main components, cyclic oligomers. The results are shown in FIG. 4.

Figure 4:
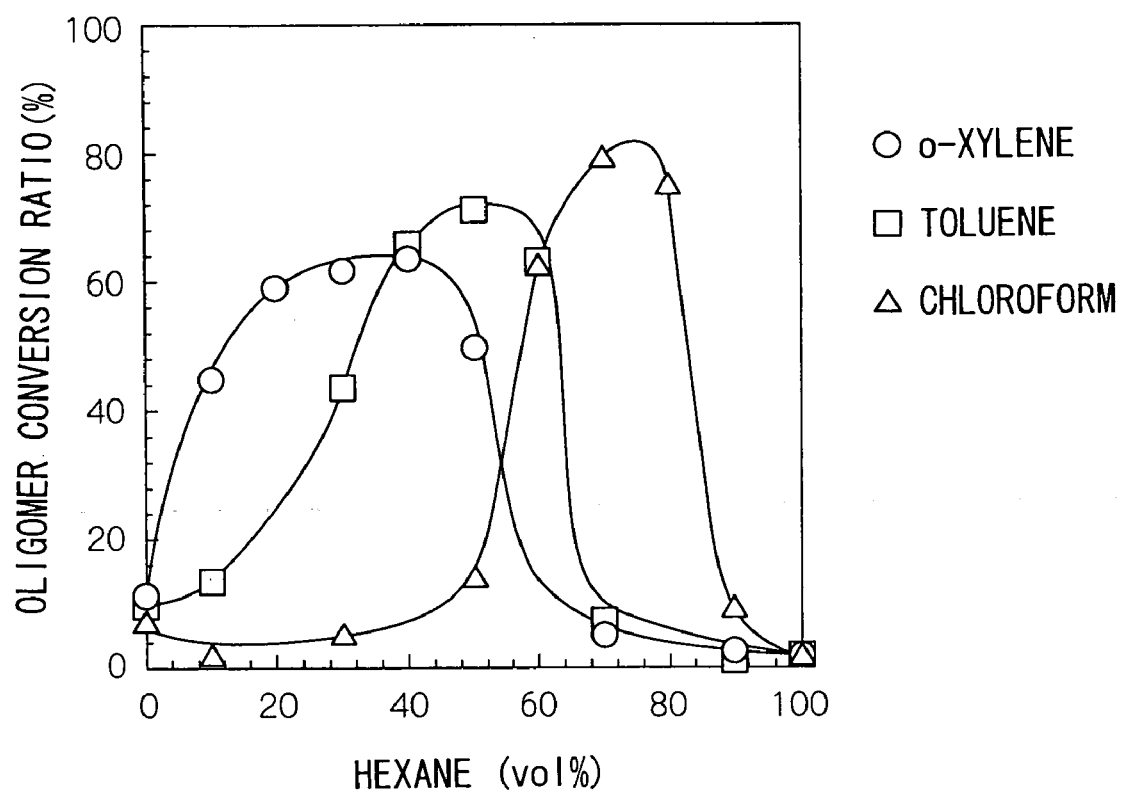
FIG. 4 is a graph showing a relationship between organic solvent composition and oligomer conversion ratio in Example 4.

As illustrated in FIG. 4, in the mixed solvent wherein hexane and chloroform were mixed at a ratio of 7 to 3 (ratio by volume), a highest conversion ratio (82%) to cyclic oligomers was obtained. In the mixed solvent wherein hexane and toluene were mixed at a ratio of 1 to 1 (ratio by volume), and the mixed solvent wherein hexane and o-xylene were mixed at a ratio of 3 to 7 (ratio by volume) also, high conversion ratios to cyclic oligomers were obtained (the conversion ratios being 72% and 65%, respectively).

Example 5

Depolymerization of poly(DL-lactic acid) (PDLLA)

To 2 ml of a mixed solvent wherein ethanol was added, into 1% by volume, to a mixture wherein chloroform and hexane were mixed at a ratio of 3 to 7 (ratio by volume) were added 10 mg of PDLLA (Mw=140,000) and 10 mg (100%) of the immobilized enzyme, Lipozyme RM IM. This was put into a small pressure-resistant test tube with a screw cap, in which a magnetic stirrer was put. The tube was purged with argon, and then the solution was stirred at 60° C. to depolymerize PDLLA. The yield of the resultant oligomer was measured by GPC with the passage of time. Additionally, depolymerization was conducted in the same way except that the added amount of Lipozyme RM IM was changed to 30 mg (300%).

Figure 5:
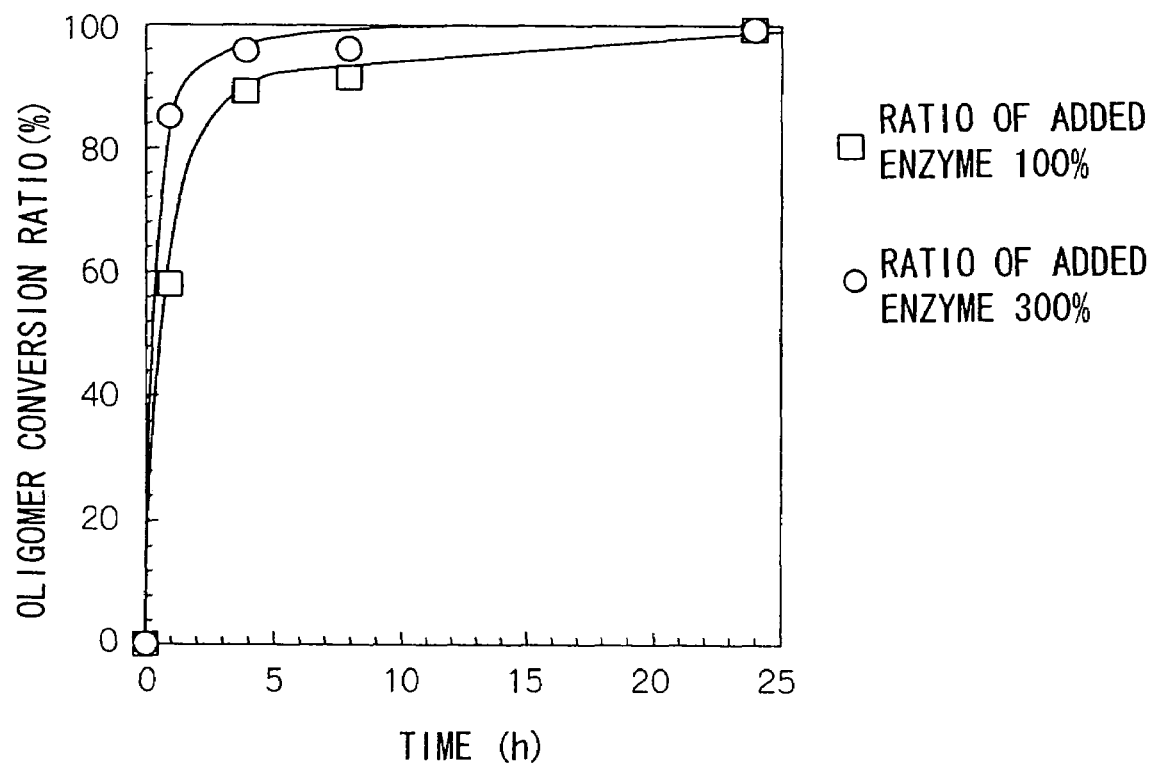
FIG. 5 is a graph showing a change over time in oligomer conversion ratio in depolymerization in Example 5.

FIG. 5 shows the oligomer conversion ratio in the depolymerization over time. As illustrated in FIG. 5, in both cases wherein the amounts of the immobilized enzyme were 100% and 300%, respectively, the depolymerization rate was remarkably raised by the addition of the small amount of ethanol. In about 4 hours, the oligomer conversion ratio reached 90% or more. From the result of the GPC analysis, the moiety of the original polymer vanished completely.

Figure 6:
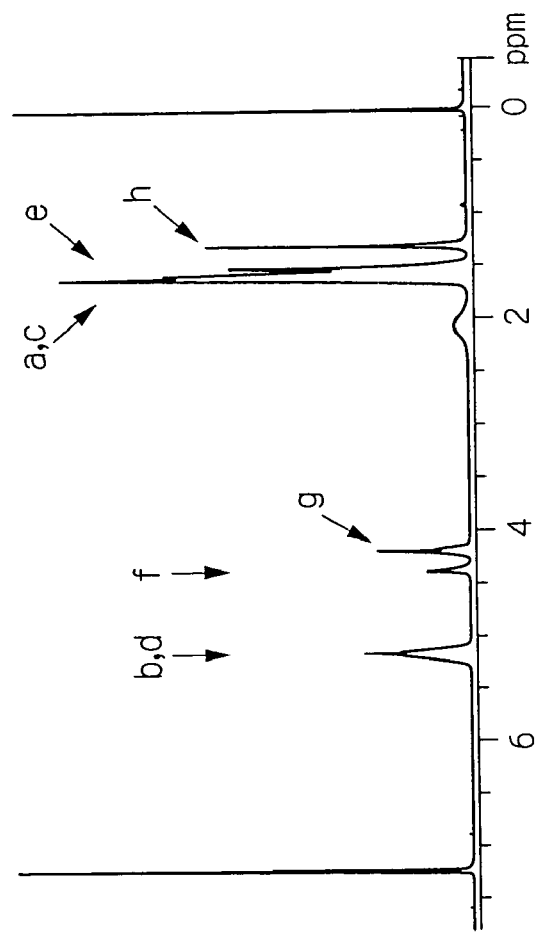
FIG. 6 is a graph showing the $^1$H-NMR of a depolymerization product in Example 5.

FIG. 6 shows the $^1$H NMR of the resultant oligomers. It was found that the resultant oligomers were linear, and the linear oligomers were produced as substantially complete monoethyl ester products. The main oligomer thereof was a septimer wherein n was 5.

Example 6

Depolymerization of Heterotactic poly(DL-lactic acid) (PDLLA)

There were weighed 10 mg of heterotactic PDLLA (Mw=140,000), 90 mg of the immobilized enzyme, Lipozyme RM IM, and 2 ml of o-xylene, and then they were put into a small pressure-resistant test tube with a screw cap, in which a magnetic stirrer was put. The tube was purged with argon, and then the solution was stirred at 65° C. for 24 hours. Next, thereto was added a small amount of chloroform, and then the immobilized lipase which was insoluble was filtrated off. An evaporator was used to concentrate the solvent from the filtrate under reduced pressure to yield oligomers including, as main components, cyclic octamers (the oligomers including linear oligomers also, and the main components thereof being the octamers) at a conversion ratio of 97% (Mn=510, Mw/Mn=1.5). FIG. 7 shows the MALDI-TOF MS of the depolymerization product. In FIG. 7, C8 represents a cyclic oligomer wherein the number of lactic acid units was 8 (m=8), and L8 represents a linear oligomer wherein the number of lactic acid units was 8 (n=8). In the graph, Li means a product wherein Li ions were added to molecule ions in the measurement of the MALDI-TOF MS in order to make analysis easy.

$^1$H-NMR: (300 MHz, CDCl$_3$) δ=1.4-1.7 (m, 3H, CH$_3$), 5.1-5.3 ppm (m, 1H, CH)

Heterotactic PDLLA was depolymerized in the same way except that Lipozyme RM IM was changed to Novozym 435. As a result, oligomers including, as main components, cyclic oligomers were yielded at a conversion ratio of 70%.

As described above, it was confirmed that good oligomerization was attained by the combination of heterotactic PDLLA with o-xylene.

Example 7

Depolymerization of Syndiotactic poly(DL-lactic acid)

There were weighted 5 mg of PDLLA (Mw=140,000), 30 mg of the immobilized enzyme, Lipozyme RM IM, and 1 ml of o-xylene, and they were put into a small pressure-resistant test tube with a screw cap, in which a magnetic stirrer was put. The tube was purged with argon, and then the solution was stirred at 50° C. for a day. Next, thereto was added a small amount of chloroform, and then the immobilized lipase which was insoluble was filtrated off. An evaporator was used to concentrate the solvent from the filtrate under reduced pressure to yield oligomers including, as main components, cyclic oligomers, at a conversion ratio of 100%.

Oligomers including, as main components, cyclic oligomers were obtained at a conversion ratio of 100% by use of Novozym 435 also.

Example 8

Depolymerization of poly(L-lactic acid-ε-caprolactone) Copolymer [P(LLA-CL)]

Figure 8:
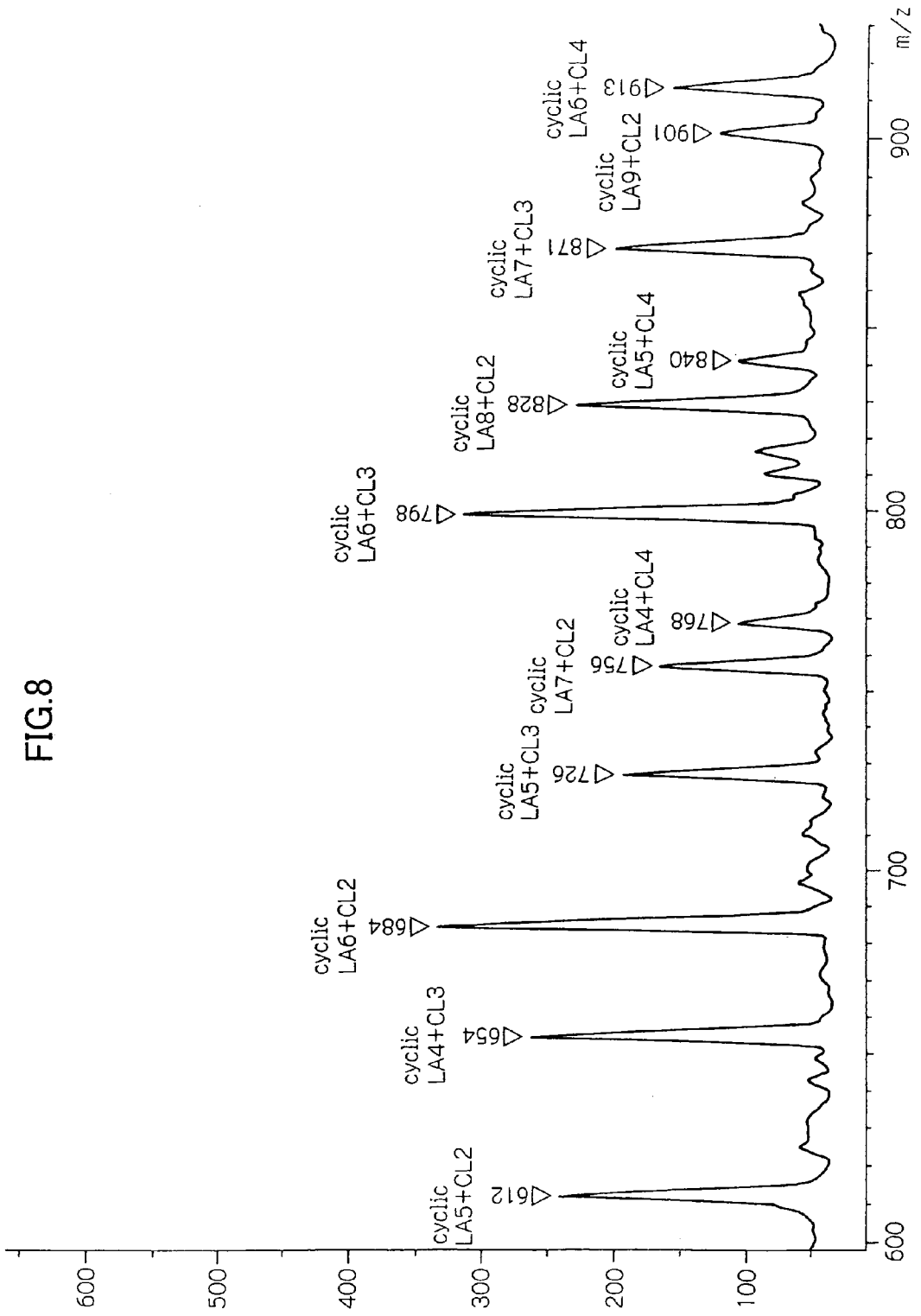
FIG. 8 is a graph showing the MALDI-TOF MS of a depolymerization product in Example 8.

There were weighed 30 mg of P(LLA-CL) (Mn=50,000; mole ratio of L-LA to CL: 6/4), 30 mg of Novozym 435, 1 ml of toluene, and water, the amount thereof being 10% by mass of P(LLA-CL), and then they were put into a small pressure-resistant test tube with a screw cap, in which a magnetic stirrer was put. The tube was purged with argon, and then the solution was stirred at 70° C. for a day. Next, thereto was added a small amount of chloroform, and then the immobilized lipase which was insoluble was filtrated off. An evaporator was used to concentrate the solvent from the filtrate under reduced pressure, so as to yield an oligomer mixture including, as main components, cyclic oligomers, wherein the polymerization degree thereof was 4 to 10, at a conversion ratio of about 100%. The composition ratio between L-LA and CL in the oligomers was distributed substantially in accordance with the composition ratio therebetween in the charged polymer. FIG. 8 shows the MALDI-TOF MS (Na$^{30}$ adduct) of the depolymerization product. In FIG. 8, LA represents lactic units in the oligomers, and CL represents caprolactone units in the oligomers. The number at the side of LA or CL represents the number of the units thereof.

$^1$H-NMR: (300 MHz, CDCl$_3$) δ=1.4-1.7 (LA, CH$_3$; CL, CH$_2$CH$_2$CH$_2$), 2.3-2.5 (LA, CH$_2$C=O), 4.05-4.2 (LA, OCH$_2$), 5.1-5.3 (LA, CH)

The same results were obtained in the case that o-xylene, which was a solvent other than toluene, was used. In the case that Novozym 435 was used, degradation advanced in acetonitrile also.

In the case that the used enzyme was any one of Novozym 435 and Lipozyme RM IM, cyclic oligomers were rapidly produced. Regarding the composition of the degradation oligomers, the cyclic oligomers were produced to have the composition corresponding basically to the composition ratio between L-LA and CL. In the case of using Novozym 435, it was found that a slight difference that the production of dicaprolactone, which was a cyclic dimer of CL was generated in the copolymer having a high CL content.

The depolymerization temperature may be 70 to 100° C. Within this range, largely different results are not obtained.

It is desired that the CL content in P(LLA-CL) was 20% or more by mole. If the content is smaller than this, the depolymerization degree lowers so that the molecular weight of the oligomers becomes high and the molecular weight distribution becomes broad. Table 1 shows typical examples thereof. About conditions for the depolymerization, a solution of 30 mg of P(LLA-CL), 30 mg of Novozym 435 and 1 ml of toluene was stirred at 70° C. for 24 hours.

TABLE 1

| Mole ratio of L-LA to Cl in P(LLA-CL) | Number-average molecular weight of oligomers (Mn) | Molecular weight variance (Mw/Mn) |
|---|---|---|
| 60/40 | 480 | 6.5 |
| 68/32 | 680 | 7.6 |
| 78/22 | 720 | 8.0 |
| 84/16 | 940 | 13.2 |
| 87/73 | 960 | 16.9 |

Effects of use of various solvents onto the molecular weight of the degradation product are shown in Table 2. Regarding conditions for the depolymerization, a solution of 20 mg of P(LLA-CL) (mole ratio of L-LA to CL: 6/4, Mn=50,000 and Mw/Mn=1.8) and 20 mg of Novozym 435, 8 mg of water and 1 ml of each organic solvent was stirred at each temperature shown in Table 2 for 24 hours.

TABLE 2

| Organic solvent | Depolymerization temperature (° C.) | Number-average molecular weight of oligomers (Mn) | Molecular weight variance (Mw/Mn) |
|---|---|---|---|
| Acetonitrile | 70 | 640 | 6.3 |
| Toluene | 70 | 440 | 5.4 |
| o-Xylene | 70 | 390 | 4.6 |
| 1,4-Dioxane | 70 | 1100 | 6.6 |
| Tetrachloromethylene | 70 | 630 | 7.6 |
| Hexane | 60 | 1180 | 7.2 |
| Tetrahydrofuran | 60 | 1300 | 4.4 |
| Isopropyl ether | 60 | 480 | 8.3 |

Example 9

Depolymerization of poly(L-lactic acid-trimethylenecarbonate) Copolymer [P(LLA-TMC)]

There were weighed 20 mg of P(LLA-TMC) (Mn=17,000; mole ratio of L-LA to TMC: 6/4), 1 mL of o-xylene, 8 mg of water and 20 mg of Novozym 435, and then they were put into a small pressure-resistant test tube with a screw cap, in which a magnetic stirrer was put. The tube was purged with argon, and then the solution was stirred at 70° C. for 2 days. Next, thereto was added a small amount of chloroform, and then the immobilized lipase which was insoluble was filtrated off. An evaporator was used to concentrate the solvent from the filtrate under reduced pressure to yield oligomers including, as main components, cyclic oligomers, at a conversion ratio of 100%.

Example 10

Depolymerization of poly(L-lactic acid-trimethylenecarbonate) Copolymer [P(LLA-TMC)]

Figure 9:
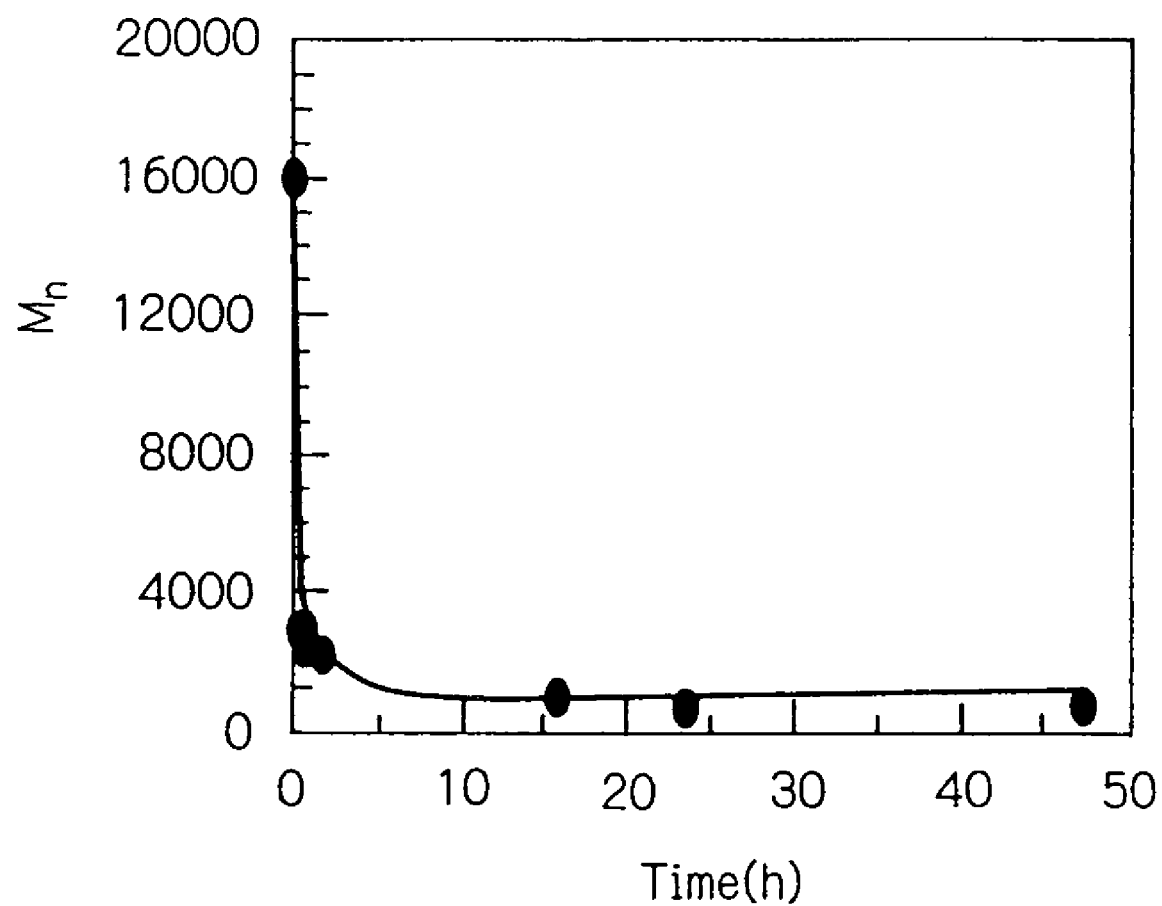
FIG. 9 is a graph showing a change over time in molecular weight in depolymerization in Example 10.
Figure 10:
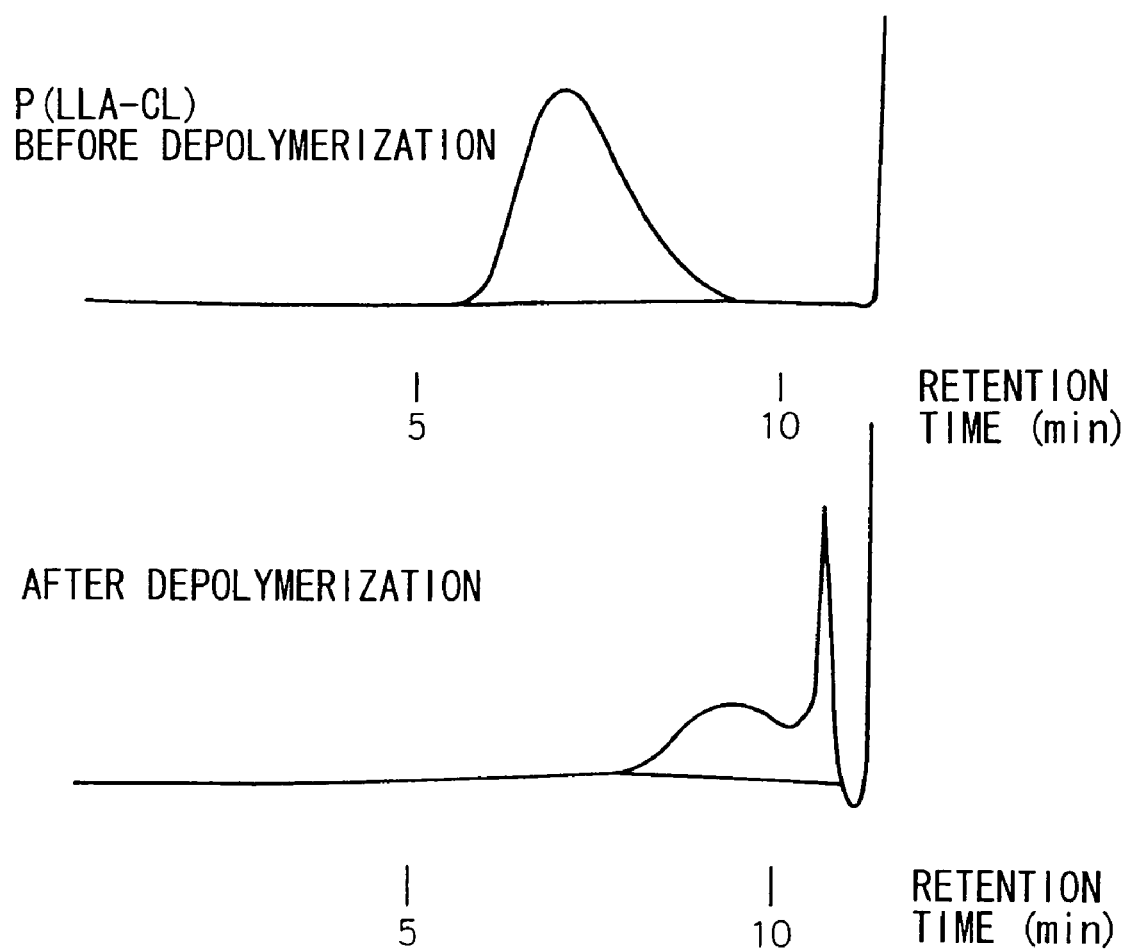
FIG. 10 is a graph showing a change in GPC before and after depolymerization in Example 11.

There were weighed 20 mg of P(LLA-TMC) (Mn=16,000; mole ratio of L-LA to TMC: 67/33), 1 ml of toluene, 20 mg of Novozym 435 and 8 mg of water, and then they were put into a small pressure-resistant test tube with a screw cap, in which a magnetic stirrer was put. The tube was purged with argon, and then the solution was stirred at 70° C. for a day. Next, thereto was added a small amount of chloroform, and then the immobilized lipase which was insoluble was filtrated off. An evaporator was used to concentrate the solvent from the filtrate under reduced pressure to yield oligomer mixture including LA and TMC units (molecular weight Mn=6,000) at a conversion ratio of 75%. The oligomer mixture included cyclic oligomers as the main components thereof, and included a slight amount of linear oligomers. FIG. 9 shows a change in the molecular weight of the oligomers from P(LLA-TMC) over time (a change in the depolymerization over time).

Example 11

Depolymerization of poly(L-lactic acid-ε-caprolactone) Copolymer [P(LLA-CL)], Using a Supercritical Fluid There were weighed 25 mg of P(LLA-CL) (Mn=50,000; the mole ratio of L-LA to CL: 7/3), 10 mg of the immobilized enzyme Novozym 435, 12 mg of water, and they were put into a 10-ml stainless steel pressure-resistant reaction tube. Next, liquefied carbon dioxide was filled thereinto at 18 MPa. In the supercritical carbon dioxide, the solution was stirred with a stirrer at 70° C. and 18 MPa for 24 hours to degrade P(LLA-CL). After the end of the reaction, the reaction tube was cooled with a dry ice-methanol bath and a cock for introducing gas was opened to discharge carbon dioxide gas gradually. After the pressure was returned to normal pressure. A small amount of chloroform was added to the degradation product remaining in the reaction tube, and then the immobilized lipase which was insoluble was filtrated off with celite. An evaporator was used to concentrate the solvent from the filtrate under reduced pressure, so as to yield oligomers which were composed of L-LA and CL units and included cyclic

Example 12

Re-polymerization of the Re-polymerizable Oligomer Mixture Obtained in Example 1

Figure 11:
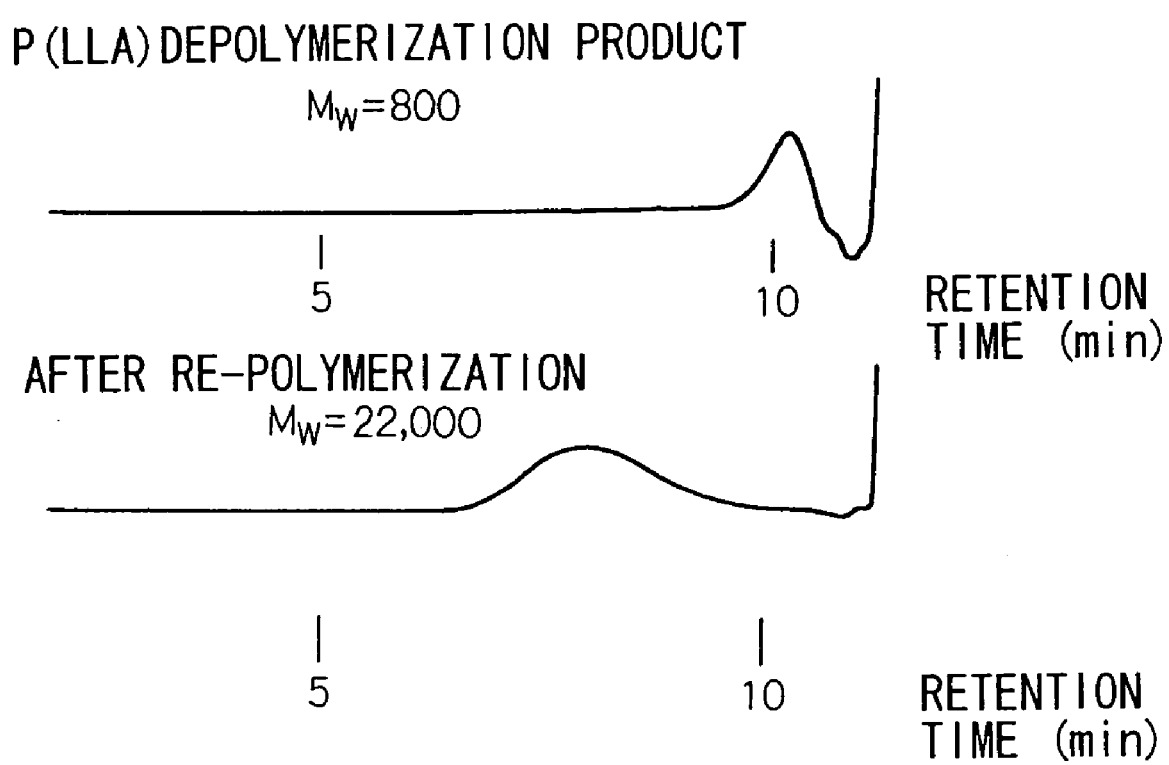
FIG. 11 is a graph showing a change in GPC before and after depolymerization in Example 12.

To 50 mg of the re-polymerizable oligomer mixture obtained in Example 1 (enzymatic depolymerization of PLLA (Mn=110,000)) was added 0.25 mg of $SnCl_2 \cdot 2H_2O$/p-$TSA \cdot H_2O$ (mole ratio: 1/1), and then the mixture was polymerized at 180° C. and a reduced pressure of 10 mmHg for 10 hours. After the end of the reaction, a small amount of chloroform was added thereto so as to dissolve the resultant. This was added to hexane/ether (1/1, v/v) so as to purify the polymer by a reprecipitation method, wherein the polymer was precipitated. In this way, PLLA having a molecular weight (Mw) of about 22,000 was yielded. FIG. 11 shows a change in GPC before and after the re-polymerization.

Example 13

Re-polymerization of the Re-polymerizable Oligomer Mixture Obtained in Example 6

To 20 mg of the re-polymerizable oligomer mixture obtained in Example 6 (the depolymerization of heterotactic PDLLA (Mw=140,000)) was added 2 mg of lipase PS, and then the mixture was polymerized at 85° C. and a reduced pressure of 40 mmHg for 5 days. After the end of the reaction, a small amount of chloroform was added thereto and the immobilized lipase which was insoluble was filtrated off. This was added to hexane/ether (1/1, v/v) so as to purify the polymer by a reprecipitation method, wherein the polymer was precipitated. In this way, PDLLA having a molecular weight (Mw) of about 20,000 was yielded.

Example 14

Re-polymerization of the Re-polymerizable Oligomer Mixture Obtained in Example 6

Figure 12:
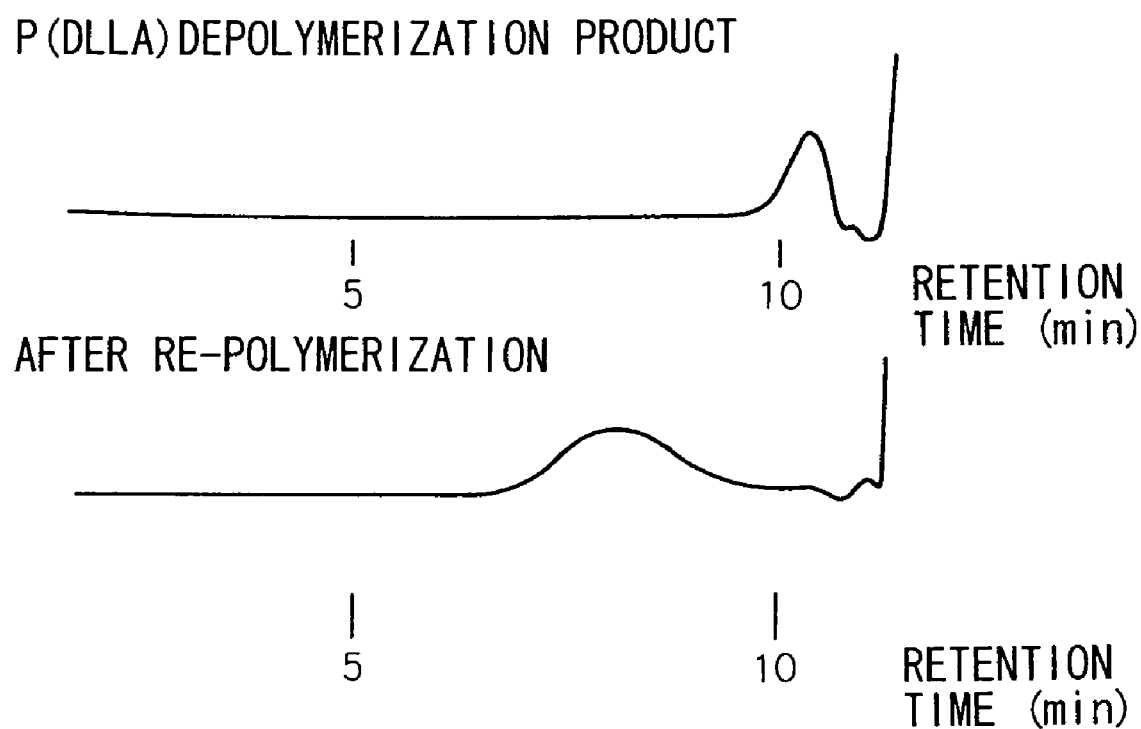
FIG. 12 is a graph showing a change in GPC before and after depolymerization in Example 14.

To 400 mg of the re-polymerizable oligomer mixture solution obtained in Example 6 (the depolymerization of heterotactic PLLA (Mn=140,000)) was added 2 mg of $SnCl_2 \cdot 2H_2O$/p-$TSA \cdot H_2O$ (mole ratio: 1/1), and then the oligomer mixture was polymerized at 180° C. and a reduced pressure of 10 mmHg for 10 hours. After the end of the reaction, a small amount of chloroform was added thereto so as to dissolve the resultant. This was added to hexane/ether (1/1, v/v) so as to purify the polymer by a reprecipitation method, wherein the polymer was precipitated. In this way, PDLLA having a molecular weight (Mw) of about 25,000 was yielded. FIG. 12 shows a change in GPC before and after the re-polymerization.

Example 15

Figure 13:
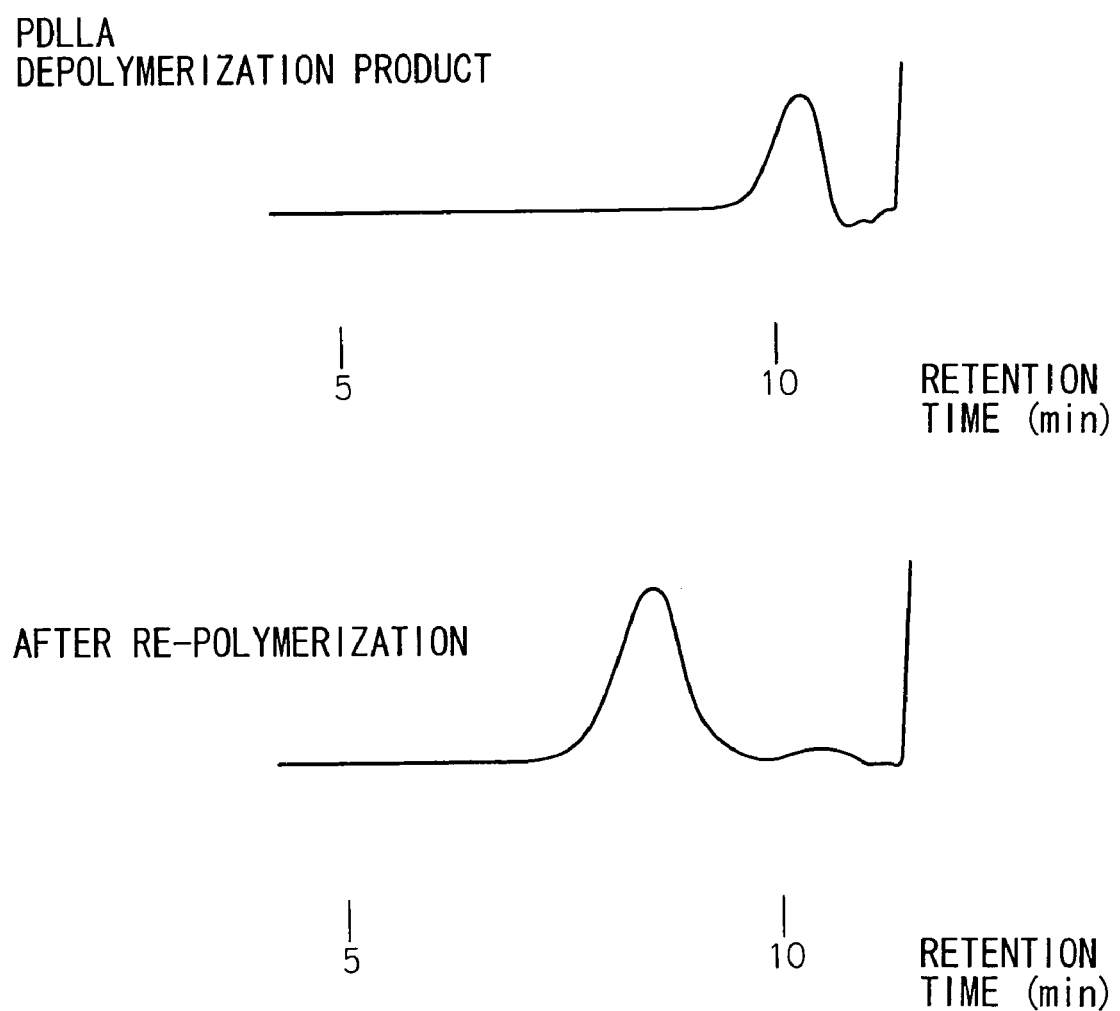
FIG. 13 is a graph showing a change in GPC before and after depolymerization in Example 15.

To 400 mg of the linear oligomers obtained in Example 5, the terminals of which were ethyl esters, was added 0.4% by mass of $SnCl_2 \cdot 2H_2O$/p-$TSA \cdot H_2O$ (mole ratio: 1/1). The oligomers were then polymerized at 180° C. and a reduced pressure of 10 mmHg while the solution was stirred. After the end of the reaction, a small amount of chloroform was added thereto so as to dissolve the resultant. This was added to hexane/ether (1/1, v/v) so as to purify the polymer by a reprecipitation method, wherein the polymer was precipitated. In this way, PLLA having a molecular weight (Mw) of about 20,000 was yielded. FIG. 13 shows a change in GPC before and after the re-polymerization. The yield (polymer conversion ratio) was 14.3%.

Example 16

Re-polymerization of the Re-polymerizable Oligomer Mixture Obtained in Example 8

Figure 14:
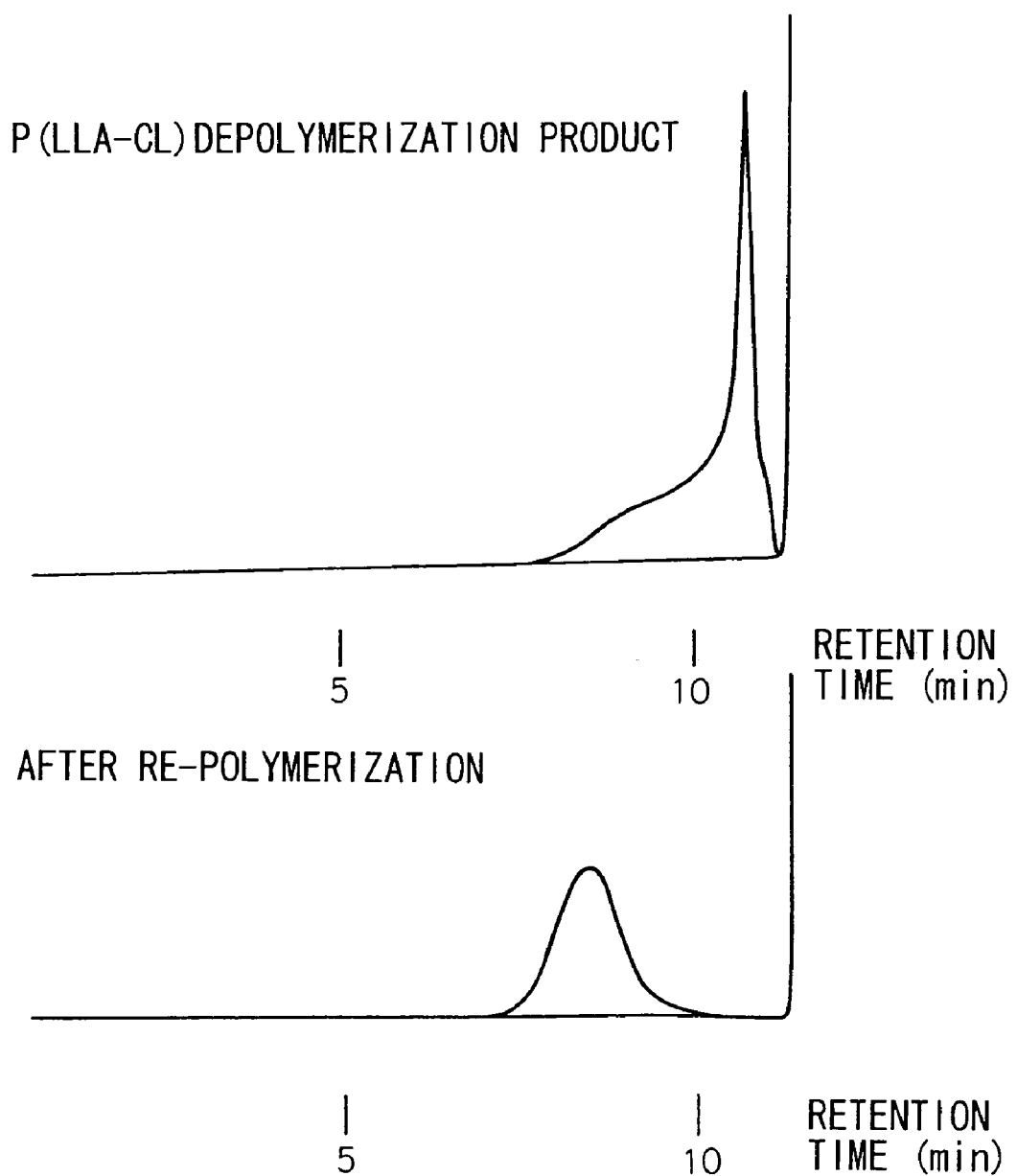
FIG. 14 is a graph showing a change in GPC before and after depolymerization in Example 16.

Into 1 ml of toluene was dissolved 300 mg of the re-polymerizable oligomer mixture obtained in Example 8 [the depolymerization of P(LLA-CL) (Mn=50,000, mole ratio of L-LA to CL: 6/4)], and thereto was added 30 mg of the immobilized enzyme Novozym 435. The resultant was subjected to reflux in a reaction flask equipped with a Dean-Stark trap at 70° C. and a reduced pressure of 140 mmHg for 6 hours so as to polymerize the oligomer mixture. After the end of the reaction, a small amount of chloroform was added thereto so as to filtrate off the immobilized lipase which was insoluble. In this way, a regenerated copolymer P(LLA-CL) (mole ratio of L-LA to CL: 6/4) was substantially quantitatively obtained. The molecular weight (Mw) obtained by gel permeation chromatography (GPC) was about 20,000. FIG. 14 shows a change in GPC before and after the re-polymerization.

INDUSTRIAL APPLICABILITY

The depolymerization process of polylactic acid and the polymerization process of the invention, using a hydrolase, may be performed by a simple operation by use of one pot, is mild in reaction conditions, and consumes low energy. In the case that the depolymerization is conducted by chemical degradation or thermal degradation, both ends of a generated low molecular weight compound is irregular and such compound cannot be re-polymerized into a polymer. However, according to the depolymerization of the invention, a re-polymerizable oligomer mixture is generated. The oligomer mixture is easily re-polymerized into a polymer in the presence of a hydrolase or in a chemically synthetic manner. Furthermore, the hydrolase used to conduct the depolymerization or the polymerization can be collected and repeatedly used. The invention has an advantageous point that a decrease in the activity of the enzyme is not substantially caused at this time. Accordingly, the invention makes it possible to construct a complete-cycle type polymer material using system which is environmentally acceptable and is capable of reusing carbon resources completely. Thus, the industrial utility value of the invention is extremely high.

What is claimed is:

1. A depolymerizing process of polylactic acid, wherein the polylactic acid is depolymerized in the presence of a hydrolase that is a lipase in an organic solvent, thereby producing a re-polymerizable oligomer.

2. A depolymerizing process of polylactic acid, wherein the polylactic acid is depolymerized in the presence of a hydrolase in a supercritical fluid, thereby producing a re-polymerizable oligomer.

3. The depolymerizing process of polylactic acid according to claim 1, wherein the polylactic acid is poly(L-lactic acid).

4. The depolymerizing process of polylactic acid according to claim 2, wherein the polylactic acid is poly(L-lactic acid).

5. The depolymerizing process of polylactic acid according to claim 1, wherein the polylactic acid is poly(DL-lactic acid).

6. The depolymerizing process of polylactic acid according to claim 2, wherein the polylactic acid is poly(DL-lactic acid).

7. The depolymerizing process of polylactic acid according to claim 1, wherein the polylactic acid is a polylactic acid copolymer.

8. The depolymerizing process of polylactic acid according to claim 2, wherein the polylactic acid is a polylactic acid copolymer.

9. The depolymerizing process of polylactic acid according to claim 2, wherein the hydrolase is lipase.

* * * * *